(12) United States Patent
Saint-Remy

(10) Patent No.: US 8,999,346 B2
(45) Date of Patent: Apr. 7, 2015

(54) IMMUNOGENIC CONTROL OF TUMOURS AND TUMOUR CELLS

(75) Inventor: Jean-Marie Saint-Remy, Grez-Doiceau (BE)

(73) Assignees: Life Sciences Research Partners VZW, Leuven (BE); Katholieke Universiteit Leuven, Leuven (BE)

( * ) Notice: Subject to any disclaimer, the term of this patent is extended or adjusted under 35 U.S.C. 154(b) by 176 days.

(21) Appl. No.: 12/735,740

(22) PCT Filed: Feb. 16, 2009

(86) PCT No.: PCT/EP2009/051804
§ 371 (c)(1),
(2), (4) Date: Aug. 13, 2010

(87) PCT Pub. No.: WO2009/101205
PCT Pub. Date: Aug. 20, 2009

(65) Prior Publication Data
US 2011/0002903 A1    Jan. 6, 2011

Related U.S. Application Data

(60) Provisional application No. 61/035,856, filed on Mar. 12, 2008.

(30) Foreign Application Priority Data

Feb. 14, 2008 (EP) ..................................... 08447011

(51) Int. Cl.
*A61K 38/00* (2006.01)
*A61K 39/00* (2006.01)
*A61K 39/385* (2006.01)
*C07K 14/47* (2006.01)
*C12N 9/02* (2006.01)

(52) U.S. Cl.
CPC ........... *A61K 39/0011* (2013.01); *A61K 39/385* (2013.01); *C07K 14/4748* (2013.01); *C12N 9/0036* (2013.01); *A61K 39/00* (2013.01); *A61K 2039/5158* (2013.01); *A61K 2039/53* (2013.01); *A61K 2039/57* (2013.01); *A61K 2039/6012* (2013.01); *C07K 2319/00* (2013.01)

(58) Field of Classification Search
CPC ........... A61K 2300/00; A61K 39/0011; A61K 39/00; A61K 38/00; C12N 15/1135; C12Q 1/6883
See application file for complete search history.

(56) References Cited

U.S. PATENT DOCUMENTS

| | | | |
|---|---|---|---|
| 4,886,782 A | 12/1989 | Good et al. | |
| 5,633,234 A | 5/1997 | August et al. | |
| 5,863,528 A | 1/1999 | Hawley et al. | |
| 6,602,509 B1 | 8/2003 | Saint-Remy et al. | |
| 6,759,046 B1 | 7/2004 | Gaudernack et al. | |
| 7,157,089 B1 | 1/2007 | Mizzen et al. | |
| 2003/0049723 A1 | 3/2003 | Zhang et al. | |
| 2003/0104570 A1 | 6/2003 | Cabezon Silva et al. | |
| 2003/0129205 A1 | 7/2003 | Saint-Remy et al. | |
| 2004/0077045 A1 | 4/2004 | Zhang et al. | |
| 2005/0107256 A1* | 5/2005 | Barnwell et al. | 504/117 |
| 2005/0196386 A1 | 9/2005 | Blazar et al. | |
| 2005/0202044 A1 | 9/2005 | Mizzen et al. | |
| 2006/0211091 A1 | 9/2006 | Zhang et al. | |
| 2006/0269561 A1 | 11/2006 | Paterson et al. | |
| 2007/0160620 A1 | 7/2007 | Mizzen et al. | |
| 2010/0203083 A1 | 8/2010 | Lux et al. | |
| 2010/0330088 A1* | 12/2010 | Saint-Remy | 424/134.1 |
| 2011/0002903 A1 | 1/2011 | Saint-Remy | |
| 2011/0110964 A1* | 5/2011 | Saint-Remy | 424/185.1 |
| 2011/0111502 A1* | 5/2011 | Saint-Remy | 435/377 |
| 2012/0009678 A1* | 1/2012 | Saint-Remy | 435/375 |

FOREIGN PATENT DOCUMENTS

| | | |
|---|---|---|
| JP | 2004-147649 | 5/2004 |
| WO | WO 93/08279 | 4/1993 |
| WO | WO 99/58552 | 11/1999 |
| WO | WO 9958552 A2 * | 11/1999 |
| WO | WO 01/70263 | 9/2001 |
| WO | WO 02/00892 | 1/2002 |
| WO | WO 02/095051 | 11/2002 |
| WO | WO 2004/018667 | 3/2004 |
| WO | WO 2004/024766 | 3/2004 |
| WO | WO 2005/012502 | 2/2005 |
| WO | WO 2005/039613 | 5/2005 |
| WO | WO 2005/086781 | 9/2005 |
| WO | WO 2006/059529 | 6/2006 |
| WO | WO 2007/104715 | 9/2007 |
| WO | WO 2008/017517 | 2/2008 |
| WO | WO 2009/100505 | 8/2009 |

(Continued)

OTHER PUBLICATIONS

Written Description Training Materials (http://www.uspto.gov/web/menu/written.pdf).*
(Mach et al, Annu Rev Immunol, 1996, 14:301-331; specifically p. 302, see "MHC Class II Regulation and the Control of the Immune Response").*
Wang et al (Seminars in Cancer Biol, 2006, 16:73-79).*
Teuku et al (Protein Science, 2006, 15:1945-1950).*
Park et al (Cell, 2006, 127:369-382).*
(Credo Reference, 2012).*
Thomson et al (J of Virol, 1998, 72:2246-2252).*
Fomenko et al, Biochemistry, 2003, 42:11214-11225.*
International Search Report for PCT/BE2008/000010, mailed Jul. 2, 2008.
Written Opinion of the International Searching Authority for PCT/BE2008/000010, mailed Jul. 2, 2008.
International Search Report for PCT/EP2009/051806, mailed Aug. 11, 2009.

(Continued)

*Primary Examiner* — Sean Aeder
*Assistant Examiner* — Julie Wu
(74) *Attorney, Agent, or Firm* — Nixon & Vanderhye P.C.

(57) ABSTRACT

The present invention relates to the use of immunogenic peptides comprising a T-cell epitope derived from a tumour-associated antigen and a redox motif such as C-(X)2-[CST] or [CST]-(X)2-C in the treatment of a tumour or in the treatment or prevention of a tumour relapse, and in the manufacture of medicaments therefore.

9 Claims, No Drawings

(56) References Cited

FOREIGN PATENT DOCUMENTS

| | | |
|---|---|---|
| WO | WO 2009/101204 | 8/2009 |
| WO | WO 2009/101205 | 8/2009 |
| WO | WO 2009/101206 | 8/2009 |
| WO | WO 2009/101207 | 8/2009 |
| WO | WO 2009/101208 | 8/2009 |

OTHER PUBLICATIONS

Written Opinion of the International Searching Authority for PCT/EP2009/051806, mailed Aug. 11, 2009.
International Search Report for PCT/EP2009/051808, mailed Feb. 18, 2010.
International Search Report for PCT/EP2009/051803, mailed Aug. 11, 2009.
Zhao et al, "Activated CD4+CD25+ T cells selectively kill B Lymphocytes", Blood, vol. 107, No. 10; pp. 3925-3932; May 15, 2006.
International Search Report for PCT/EP2009/051804, mailed Aug. 11, 2009.
Written Opinion for PCT/EP2009/051804, mailed Aug. 11, 2009.
Aleksza, M. et al., "Altered cytokine expression of peripheral blood lymphocytes in polymyositis and dermatomyositis", Ann. Rheum. Dis., vol. 64, (2005), pp. 1485-1489.
Bolivar, J. et al, "Molecular cloning of a zinc finger autoantigen transiently associated with interphase nucleolus and mitotic centromeres and midbodies. Orthologous proteins with nine CXXC motifs highly conserved form nematodes to humans", J. Biol, Chem., vol. 274, (1999), pp. 36456-36464.
Braun, M.Y. et al., "Acute rejection in the absence of cognate recognition of allograft by T cells", J. Immunol., vol. 166, No. 8, (2001), pp. 4879-4883.
Brinster, C. et al., "Costimulatory effects of IL-1 on the expansion/differentiation of CD4+CD25+Foxp3+ and CD4+CD25+Foxp3- T cells", J. Leukoc. Biol., vol. 84, (2008), pp. 480-487.
Cao, O. et al, Prevention of gene transfer-induced inhibitor formation by nasal administration of human F.IX T cell epitope in a murine model of hemophilia B., Blood, vol. 104, (2004), pp. 121A-122A.
Chen, T. C. et al., Induction of dominant transplantation tolerance by an altered peptide ligand of the male antigen Dby., J Clin. Invest., vol. 113, No. 12, (2004), pp. 1754-1762.
Davids, B.J. et al., A new family of giardial cysteine-rich non-VSP protein genes and a novel cyst protein, Plos. One., vol. 1, (2006), e44.
De La Cruz, V.F. et al., "The immunologic significance of variation within malaria circumsporozoite protein sequences", J. Immunol., vol. 142, (1989), pp. 3568-3575.
Eberl, G. et al., "Tissue-specific segregation of CD1d-dependent and CD1d-independent NK T cells", J. Immunol., vol. 162, (1999), pp. 6410-6419.
Dobrzynski, E. et al, "Prevention of cytotoxic T lymphocyte responses to factor IX-expressing hepatocytes by gene transfer-induced regulatory T cells", Proc. Natl. Acad Sci. U.S.A., vol. 103, (2006), pp. 4592-4597.
Fomenko, D.E. et al., "Identity and functions of CxxC-derived motifs", Biochemistry, vol. 42, (2003), pp. 11214-11225.
Geluk, A. et al., "HLA-DR binding analysis of peptides from islet antigens in IDDM", Diabetes, vol. 47, (1998), pp. 1594-1601.
Gross, D.A. et al., "Simple conditioning with monospecific CD4+CD25+ regulatory T cells for bone marrow engraftment and tolerance to multiple gene products", Blood, vol. 108, No. 6, (2006), pp. 1841-1848.
Grossman, W.J., et al, "Differential expression of granzymes A and B in human cytotoxic lymphocyte subsets and T regulatory cells", Blood, vol. 104, (2004), pp. 2840-2848.
Hohn, H. et al., "CD4+ tumor-infiltrating lymphocytes in cervical cancer recognize HLA-DR-restricted peptides provided by human papillomavirus-E7", J. Immunol., vol. 163, (1999), pp. 5715-5722.
Hori, S. et al., "Control of regulatory T cell development by the transcription factor Foxp3", Science, vol. 299, (2003), pp. 1057-1061.
Ise, W. et al., "Naïve CD4+ T cells exhibit distinct expression patterns in cytokines and cell surface molecules on their primary responses to varying doses of antigen", J. Immunol., vol. 168, (2002), pp. 3242-3250.
James, E. et al., HY peptides modulate transplantation responses to skin allografts, Int. Immunol., vol. 14, No. 11, (2002), pp. 1333-1342.
Joffre, O. et al., "Induction of antigen-specific tolerance to bone marrow allografts with CD4+CD25+ T lymphocytes", Blood, vol. 103, No. 11, (2004), pp. 4216-4221.
Louis, S. et al., "Contrasting CD25hiCD4+ T cells/FOXP3 patterns in chronic rejection and operational drug-free tolerance", Transplantation, vol. 81, (2006), pp. 398-407.
Maeda, M. et al., "CD1d-independent NKT cells in beta 2-microglobulin-deficient mice have hybrid phenotype and function of NK and T cells", J. Immunol., vol. 172, (2004), pp. 6115-6122.
Maynard, C.L. et al., "Regulatory T cells expressing interleukin 10 develop from Foxp3+ and Foxp3- precursor cells in the absence of interleukin 10", Nat. Immunol., vol. 8, (2007), pp. 931-941.
Qin, W. et al., "Fusion protein of CDR mimetic peptide with Fc inhibit TNF-alpha induced cytotoxicity", Mol. Immunol., vol. 43, (2006), pp. 660-666.
Roopenian, D. et al., "The immunogenomics of minor histocompatibility antigens", Immunol. Rev., vol. 190, (2002), pp. 86-94.
Saez-Borderias, A. et al, "Expression and function of NKG2D in CD4+ T cells specific for human cytomegalovirus", Eur. J. Immunol., vol. 36, (2006), pp. 3198-3206.
Stenstrom, M. et al., "Natural killer T-cell populations in C57BL/6 and NK1.1 congenic BALB.NK mice-a novel thymic subset defined by BALB.NK mice", Immunology, vol. 114, (2005), pp. 336-345.
Sundar, S.K. et al., "Generation of Epstein-Bar virus antigen-specific suppressor T cells in vitro", Int. J. Cancer, vol. 35, (1985), pp. 351-357.
Taylor, A. et al., "T regulatory cells and allergy", Microbes and Infection, vol. 7, (2005), pp. 1049-1055.
Tsuji, N.M. et al, "Antigen-specific, CD4+CD25+ regulatory T cell clones induced in Peyer's patches", Int. Immunol., vol. 15, (2003),pp. 525-534.
Voo, K.S. et al., "Functional characterization of EBV-encoded nuclear antigen 1-specific CD4+ helper and regulatory T cells elicited by in vitro peptide stimulation", Cancer Res., vol. 65, (2005), pp. 1577-1586.
Wang, R.F., "Immune suppression by tumor-specific CD4+ regulatory T-cells in cancer", Semin. Cancer Biol., vol. 16, (2006), pp. 73-79.
Wiker, H.G. et al., "Cloning, expression and significance of MPT53 for identification of secreted proteins of Mycobacterium tuberculosis", Microb. Pathog., vol. 26, (1999), pp. 207-219.
Wood, K.J. et al., "Regulatory T cells in Transplantation tolerance", Nat. Rev. Immunol., vol. 3, (2003), pp. 199-210.
Haveman, L.M. et al., Induction and capture of CD4+ cytotoxic adenoviral specific T-cells in response to pan-DR binding adenoviral epitopes toward immunotherapy, Blood, vol. 106, (2005), Abstract 3238.
Corthay, "CD4+ T Cells Cooperate with Macrophages for Specific Elimination of MHC Class II-Negative Cancer Cells", Institute of Immunology, University of Oslo and Rikshospitalet-Radiumhospitalet Medical Center, 0027 Oslo, Norway, Alexandre.Corthay@medisin.uio.no, pp. 195-208 Adv Exp Med Biol. 2007;590:195-208.
Dobrzanski, "Expanding roles for CD4T cells and their subpopulations in tumor immunity and therapy", Frontiers in Oncology, Mar. 2013, vol. 3, Article 63, pp. 1-19.
GenBank M77349.1—Skonier et al, "Human transforming growth factor-beta induced gene product (BIGH3) mRNA, complete cds", Jan. 14, 1995 (3 pages).
Tindle et al, "A "public" T-helper epitope of the E7 transforming protein of human papillomavirus 16 provides cognate help for several E7 B-cell epitopes from cervical cancer-associated human papillomavirus genotypes", Proc. Natl. Acad. Sci., vol. 88, pp. 5887-5891, Jul. 1991.
Li Pira et al, "High throughput T epitope mapping and vaccine development", 2010, Journal of Biomedicine and Technology, vol. 2010, 12 pages).

(56) References Cited

OTHER PUBLICATIONS

Crompton et al, "Advances and challenges in malaria vaccine development", 2010, The Journal of Clinical Investigation, vol. 120, pp. 4168-4178.
Sette et al, "Epitope-based vaccines: an update on epitope identification, vaccine design and delivery", 2003, Current Opinion in Immunology, vol. 15, pp. 461-470.
Roper et al, "SARS vaccines: where are we?", 2009, Expert Review of Vaccines, vol. 8, pp. 887-898.
Hsu et al, "Assessing computational amino acid—turn propensities with a phage-displayed combinatorial library and directed evolution", 2006, Structure, vol. 14, pp. 1499-1510.
European Search Report dated Jul. 17, 2013, issued in corresponding European Patent Application No. 13150813.7.
European Search Report dated Jul. 9, 2013, issued in corresponding European Patent Application No. 13151001.8.
Carlier et al, "Increased Synapse Formation Obtained by T cell Epitopes Containing a CxxC Motif in Flanking Residues Convert CD4+ T Cells into Cytolytic Effectors", Plos One, Oct. 2012, vol. 7, Issue 10, e45366, pp. 1-16.
Savoldo et al, "Generation of EBV-Specific CD4+ Cytotoxic T Cells from Virus Naïve Individuals", J. Immunol. 2002; 168:909-918.
Examination Report dated Apr. 26, 2013, issued in connection with European Patent Application No. 09 710 780.9.
Arunalacham et al, Enzymatic reduction of disulfide bonds in lysosomes: Characterization of a Gamma-interferon-inducible lysosomal thiol reductase (GILT), (2000) Proc. Natl. Acad. Sci USA, vol. 97, No. 2, 745-750.
Bower et al "Two Members of the Thioredoxin-h Family Interact with the Kinase Domain of a Brassica S Locus Receptor Kinase", (1996) The plant cell, vol. 8, 1641-1650.
Brinks et al, "Immunogenicity of Therapeutic Proteins: The Use of Animal Models", (2011) Phar res 28,2379-2385.
Capon et al, "The CD4-gp120 Interaction and Aids Pathogenesis" (1991) Ann. Rev. Immunol 9, 649-678.
Chen et al, "Glucocorticoid amplifies IL-2-dependent expansion of functional FoxP3+CD4+CD25+ T regulatory cells in vivo and enhances their capacity to suppress EAE", (2006) Eur. J. Immunol. 36, 2139-2149.
Fan et al, "Co-immunization of BALB/c mice with recombinant immunogens containing G protein fragment and chimeric CTL epitope of respiratory syncytial virus induces enhanced cellular immunity and high level of antibody response", (2005) Vaccine 23, 4453-4461.
Ge et al, "An hsp 70 fusion protein vaccine potentiates the immune response against Japanese encephalitis virus", (2007) Arch. Viral 152, 125-135.
Gentile et al, "Thyroglobulin as an autoantigen: what can we learn about immunopathogenicity from the correlation of antigenic properties with protein structure?", (2004) Immunol 112 13-25.
Haque, "Cysteinylation of MHC Class II Ligands: Peptide Endocytosis and Reduction Within APC Influences T Cell Recognition[1]", (2001) J. Immunol. 166, 4543-4551.
Harris, Prediction of murine MHC class I epitopes in a major house dust mite allergen and induction of T1-type CD8+ T cell responses, (1997) Int. Immunol., vol. 9, No. 2, 273-280.
Janssens et al, "CD4+ CD25+ T Cells Lyse Antigen-Presenting B Cells by Fas-Fas Ligand Interaction in an Epitope-Specific Manner[1]", (2003) J. Immunol. 171, 4604-4612.
Jensen, "Acidification and Disulfide Reduction Can be Sufficient to Allow Intact Proteins to Bind Class II MHC[1]", (1993) J. Immunol. 150, No. 8, 3347-3356.
Wobus et al, "Embryonic Stem Cells: Prospects for Developmental Biology and Cell Therapy", (2005) Physiol Rev 85: 635-678.
Khare et al, "HLA class II transgenic mice authenticate restriction of myelin oligodendrocyte glycoprotein-specific immune response implicated in multiple sclerosis pathogenesis", (2003) Int. Immunol. 15, No. 4, 535-546.
Maekawa et al, "Evidence for a Domain-Swapped CD4 Dimer as the Coreceptor for Binding to Class II MHC[1]", (2006) J. Immunol. 176(11), 6873-6878.
Matthias et al, "Disulfide exchange in domain 2 of CD4 is required for entry of HIV-1", (2002) Nature immunol 3, No. 8, 727-732.
Okubo et al, "Analysis of HLA-DRB1 0901-binding HPV-16 E7 helper T cell epitopeI", (2004) J Obstet Gynaecol Res. 30(2), 120-129.
Oliviera et al, "Insights into the Specificity of Thioredoxin Reductase—Thioredoxin Interactions. A Structural and Functional Investigation of the Yeast Thioredoxin System", (2010) biochemistry 49, 3317-3326.
Roep et al, "The problems and promises of research into human immunology and autoimmune disease", (2012) Nature Med 18(1) 48-53.
Santin et al, "Human Papillomavirus Type 16 and 18 E7-Pulsed Dendritic Cell Vaccination of Stage IB or IIA Cervical Cancer Patients: a Phase I Escalating-Dose Trial", (2008) J. Virol. 82, No. 4, 1968-1979.
Shi et al, "A novel plasma membrane-bound thioredoxin from soybean", (1996) Plant Mol. Biol. 32, 653-662.
Texier et al, "On the diversity and heterogeneity of $H-2^d$-restricted determinants and T cell epitopes from the major bee venom allergen", (1999) Int Immunol. 11, 1313-1325.
Weissert et al, "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis", (2001) J. Immunol. 166, 7588-7599.
Wekerle et al, "Autoimmunity's next top models", (2012) Nature Med. 18(1), 66-70.
Wu et al, "Engineering an intracellular pathway for major histocompatibility complex class II presentation of antigens", (1995) Proc. Natl. Acad. Sci. 92, 11671-11675.
Toyokawa et al, "Relative Contribution of Direct and Indirect Allorecognition in Developing Tolerance After Liver Transplantation", 2008 Liver Transpl. 14(3) 346-357.
Boisgerault et al, "Differential roles of direct and indirect allorecognition pathways in the rejection of skin and corneal transplants", (2009) Transplantation 87(1): 16-23.
Li et al, "Twisting immune responses for allogeneic stem cell therapy", (2009) World J Stem Cells 1(1), 30-35.
Batten et al, "Immune response to stem cells and strategies to induce tolerance", (2007) Phil. Trans. R. Soc. B 362, 1343-1356.
Heemskerk et al, "Adenovirus-Specific CD4+ T Cell Clones Recognizing Endogenous Antigen Inhibit Viral Replication in Vitro through Cognate Interaction", J. Immunol 2006; 177-8851-8859.

\* cited by examiner

IMMUNOGENIC CONTROL OF TUMOURS AND TUMOUR CELLS

This application is the U.S. national phase of International Application No. PCT/EP2009/051804 filed 16 Feb. 2009, which designated the U.S.; claims priority to EP Application No. 08447011.1 filed 14 Feb. 2008; and claims the benefit of U.S. Provisional No. 61/035,856 filed 12 Mar. 2008, the entire contents of each of which are hereby incorporated by reference.

FIELD OF THE INVENTION

The present invention relates to immunogenic peptides and their use in (immune) therapies for the eradication of tumours and tumour cells and prevention of tumour relapses.

BACKGROUND OF THE INVENTION

Many tumours express antigens which may serve as a target or therapy. Such antigens can be broadly divided into:
- oncogenes, such as the MAGE identified in some melanomas;
- proto-oncogenes, such as cyclin D1 expressed on soft tissues carcinomas such as those of the kidney or parathyroid, as well as in multiple myeloma;
- virus-derived proteins, such as those from the Epstein-Barr virus in some carcinomas and in some Hodgkin-type lymphomas;
- surviving factors, which are anti-apoptotic factors such as survivin or bcl2; and
- clonotypic determinants, such as idiotypic determinants derived from B cell receptor in follicular lymphomas or multiple myelomas or T cell receptor determinants in T cell malignancies.

Specific recognition of such antigens, expressed exclusively or predominantly in tumour cells, offers the potential of a selective elimination of such cells. Active immunisation with tumour-associated antigens or derivatives, or adoptive transfer of cells expanded in vitro with such tumour-associated antigens could in theory be of interest for the therapy of tumours. Over recent years, many attempts to elicit tumour-specific elimination by specific immunotherapy have been published. These included active immunisation with, for example, idiotype-derived peptides, as well as adoptive transfer of T cells expanded in vitro by exposure to tumour cells. Although very promising, these therapeutic approaches had limited success and/or were associated with a high rate of relapse. Besides, the capacity of T cells to undergo expansion in vitro remains limited, with much loss of effector cells by apoptosis induced by overstimulation. Essentially all the work carried out in the field of immunotherapy of tumours during the last 15 years has been devoted to methods to elicit cytolytic CD8+ T cells able to recognise and lyse tumour cells in a MHC class I dependent presentation of a tumour-derived antigen. The possibility of designing efficient immunotherapy through MHC class II presentation of tumour-derived peptides and CD4+ T cells has not been explored until very recently (Perez-Diez et al. (2007), Blood 109, 5346-5354). This is imputable to several factors, including the widespread belief that most tumours do not express MHC class II determinants and that the function of CD4+ T cells does not predispose them to be potent anti-tumour cells. The classical view is that CD4+ T cells can help in providing help to B cells to produce specific antibodies and that the production of IFN-gamma by Th1 CD4+ T cells could reduce angiogenesis. More recently, the requirement of CD4+ T cells as a source of IL-2 to help CD8+ T cells to acquire full maturation has been described.

Despite major advances in the field of cancer treatment, immunotherapy of tumours is still in its infancy. The potential selectivity of such immunotherapy, certainly when targeting tumour-specific antigens, is an important advantage and may eliminate the sometimes severe side effects observed with e.g. chemotherapy. Therefore, any new strategy for immunotherapeutic treatment of cancer would be welcomed.

SUMMARY OF THE INVENTION

The present invention relates to the treatment of a tumour and/or the prevention of a tumour relapse in a patient using at least one isolated immunogenic peptide comprising (i) a T-cell epitope derived from a tumour-associated antigen and (ii) a [CST]-(X)2-[CST] motif, more particularly a C-(X)2-[CST] or [CST]-(X)2-C motif.

The present invention relates in one aspect to the use of at least one isolated immunogenic peptide comprising (i) a T-cell epitope derived from a tumour-associated antigen and (ii) a [CST]-(X)2-[CST] motif, more particularly a C-(X)2-[CST] or [CST]-(X)2-C motif for the manufacture of a medicament for treating a tumour or for preventing or treating a tumour relapse.

In a further aspect, the invention also covers the use of at least one isolated immunogenic peptide comprising (i) a T-cell epitope derived from a tumour-associated antigen and (ii) a [CST]-(X)2-[CST] motif, for the manufacture of a medicament for inducing CD4+ regulatory T cells which are cytotoxic to cells presenting said tumour-associated antigen.

The invention generally relates to immunogenic peptides comprising a T-cell epitope derived from a tumour-associated antigen and (ii) a C-(X)2-[CST] or [CST]-(X)2-C motif for use in treating a tumour or for preventing or treating a tumour relapse and/or inducing CD4+ regulatory T cells which are cytotoxic to cells presenting said tumour-associated antigen.

In any of the above uses said tumour-associated antigen may be chosen from oncogenes, proto-oncogenes, viral proteins, surviving factors or clonotypic determinants.

In any of the above uses, said C-(X)2-[CST] or [CST]-(X)2-C motif in said immunogenic peptide may be adjacent to said T-cell epitope, or be separated from said T-cell epitope by a linker. In particular, said linker consists of at most 7 amino acids.

In further embodiments of the immunogenic peptide in the above uses, said C-(X)2-[CST] or [CST]-(X)2-C motif does not naturally occur within a region of 11 amino acids N-terminally or C-terminally of the T-cell epitope in the tumour-associated antigen. In particular embodiments, said C-(X)2-[CST] or [CST]-(X)2-C motif is positioned N-terminally of the T-cell epitope. Further in particular, at least one X in said [CST]-(X)2-[CST] motif is Gly, Ala, Ser or Thr; Additionally or alternatively, at least one X in the C-(X)2-[CST] or [CST]-(X)2-C motif is His or Pro. In an additional specification at least one C in the C-(X)2-[CST] or [CST]-(X)2-C motif is methylated.

In yet further embodiments of the immunogenic peptide for use in the herein described applications, the immunogenic peptide further comprises an endosomal targeting sequence. Any of the above immunogenic peptides may be produced by chemical synthesis or by recombinant expression.

A further aspect of the invention relates to methods for obtaining a population of tumour-associated antigen-specific regulatory T cells with cytotoxic properties, said methods comprising the steps of:

providing peripheral blood cells;
contacting said cells with an immunogenic peptide comprising (i) a T-cell epitope derived from a tumour-associated antigen and (ii) a [CST]-(X)2-[CST] motif, more particularly a C-(X)2-[CST] or [CST]-(X)2-C motif; and
expanding said cells in the presence of IL-2.

A further method of the invention aims at obtaining a population of tumour-associated antigen-specific regulatory T cells with cytotoxic properties, and such methods comprise the steps of:
providing an immunogenic peptide comprising (i) a T-cell epitope derived from a tumour-associated antigen and (ii) a [CST]-(X)2-[CST] motif, more particularly a C-(X)2-[CST] or [CST]-(X)2-C motif;
administering said immunogenic peptide to a subject; and
obtaining said population of tumour-associated antigen-specific regulatory T cells from said subject.

Populations of tumour-associated antigen-specific regulatory T cells with cytotoxic properties obtainable by the above methods are also part of the invention, as well as their use for the manufacture of a medicament for preventing or treating a tumour or tumour relapse.

A further aspect of the invention relates to isolated immunogenic peptides comprising a T-cell epitope from a tumour-associated antigen and, adjacent to said T-cell epitope or separated from said T-cell epitope by a linker, a [CST]-(X)2-[CST], more particularly a C-(X)2-[CST] or [CST]-(X)2-C motif.

Yet another aspect of the invention relates to the use of at least one isolated immunogenic peptide for the manufacture of a medicament for (substantially) treating or preventing a B-cell tumour or relapse of a B-cell tumour, the immunogenic peptide comprising (i) a T-cell epitope derived from said B-cell tumour idiotype and (ii) a [CST]-(X)2-[CST] motif, more particularly C-(X)2-[CST] or [CST]-(X)2-C.

The invention also encompasses the use of at least one isolated immunogenic peptide for the manufacture of a medicament for treating a T-cell tumour or for treating or preventing relapse of a T-cell tumour, the immunogenic peptide comprising (i) a T-cell epitope derived from a T-cell CDR3 of said tumour and (ii) a [CST]-(X)2-[CST] motif, more particularly C-(X)2-[CST] or [CST]-(X)2-C.

DETAILED DESCRIPTION OF THE INVENTION

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein or factor which is/are specifically recognised and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) and/or comprising T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "tumour-associated antigen" refers to any protein, peptide or antigen associated with (carried by, produced by, secreted by, etc) a tumour or tumour cell(s). Tumour-associated antigens may be (nearly) exclusively associated with a tumour or tumour cell(s) and not with healthy normal cells or may be overexpressed (e.g., 10 times, 100 times, 1000 times or more) in a tumour or tumour cell(s) compared to healthy normal cells. More particularly a tumour-associated antigen is an antigen capable of being presented (in processed form) by MHC determinants of the tumour cell. Hence, tumour-associated antigens are likely to be associated only with tumours or tumour cells expressing MHC molecules.

The term "T cell epitope" or "T-cell epitope" in the context of the present invention refers to a dominant, sub-dominant or minor T cell epitope, i.e., a part of an antigenic protein or factor that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein. In particular, a T cell epitope is an epitope bound by MHC class I or MHC class II molecules.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLA-DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells. Peptide fragments presented in the context of class I MHC molecules are recognized by CD8+ T lymphocytes (cytotoxic T lymphocytes or CTLs). CD8+ T lymphocytes frequently mature into cytotoxic effectors which can lyse cells bearing the stimulating antigen. Class II MHC molecules are expressed primarily on activated lymphocytes and antigen-presenting cells. CD4+ T lymphocytes (helper T lymphocytes or HTLs) are activated with recognition of a unique peptide fragment presented by a class II MHC molecule, usually found on an antigen presenting cell like a macrophage or dendritic cell. CD4+ T lymphocytes proliferate and secrete cytokines that either support an antibody-mediated response through the production of IL-4 and IL-10 or support a cell-mediated response through the production of IL-2 and IFN-gamma.

Functional HLAs are characterised by a deep binding groove to which endogenous as well as foreign, potentially antigenic peptides bind. The groove is further characterised by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Superposition of the structures of different HLA complexes confirmed a general mode of binding wherein peptides adopt a relatively linear, extended conformation.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N-and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids of an MHC class II T cell epitope that fit in the groove of the MHC II molecule are usually numbered P1 to P9. Additional amino acids N-terminal of the epitope are numbered P-1, P-2 and so on, amino acids C-terminal of the epitope are numbered P+1, P+2 and so on.

The term "organic compound having a reducing activity" when used herein refers to compounds, more in particular amino acid sequences, capable of reducing disulfide bonds in proteins. An alternatively used term is "redox motif".

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when used herein referring to a sequence relates to the fact that the sequence is identical to a naturally occurring sequence or is identical to part of such naturally occurring sequence. In contrast therewith the term "artificial" refers to a sequence which as such does not occur in nature. Unless otherwise specified the terms natural and artificial thus exclusively relate to a particular amino acid (or nucleotide) sequence (e.g. the sequence of the immunogenic peptide, a sequence comprised within the immunogenic peptide, an epitope sequence) and do not refer to the nature of the immunogenic peptide as such. Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation.

Motifs of amino acid sequences are written herein according to the format of Prosite (Hulo et al. (2006) *Nucleic Acids Res.* 34 (Database issue D227-D230). The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The term "homologue" when used herein with reference to the epitopes used in the context of the invention, refer to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular embodiments of homologues of an epitope correspond to the natural epitope modified in at most three, more particularly in at most two, most particularly in one amino acid.

The term "derivative" when used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilising the peptides or altering the pharmacokinetic or pharmacodynamic properties of the peptide.

The term "sequence identity" of two sequences when used herein relates to the number of positions with identical nucleotides or amino acids divided by the number of nucleotides or amino acids in the shorter of the sequences, when the two sequences are aligned. In particular embodiments, said sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" when used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

The present invention provides strategies for immunotherapy of tumour or tumour cell(s) or tumour relapses using compounds comprising a T-cell epitope derived from a tumour-associated antigen to which a motif with thioreductase activity (or shortly: redox motif) is attached. These compounds elicit tumour-associated antigen-specific CD4+ T-cells with strong capacity to induce apoptosis of tumour cells. These cytotoxic CD4+ T-cells cells can be elicited in vivo by active immunisation with these compounds or can be expanded in vitro (ex vivo) for adoptive transfer into tumour-bearing hosts.

Thus, in one aspect the invention relates isolated immunogenic peptides for use in the treatment of a tumour or for the prevention of a tumour relapse in a patient. More particularly the invention envisages the use of at least one isolated immunogenic peptide comprising (i) a T-cell epitope derived from a tumour-associated antigen and (ii) a C-(X)2-[CST] or [CST]-(X)2-C motif, for the manufacture of a medicament for treating a tumour or for preventing or treating a tumour relapse.

In a further aspect, the invention also covers the use of at least one isolated immunogenic peptide comprising (i) a T-cell epitope derived from a tumour-associated antigen and (ii) a C-(X)2-[CST] or [CST]-(X)2-C motif, for the manufacture of a medicament for inducing CD4+ regulatory T cells which are cytotoxic to cells presenting said tumour-associated antigen.

In any of the uses described hereinabove, the subject or recipient receiving said immunogenic peptide is a mammal, in particular a (non-human) primate or a human.

In any of the above uses a tumour-associated antigen may be chosen from oncogenes, proto-oncogenes, viral proteins, surviving factors or clonotypic/idiotypic determinants. Such antigens are known and accepted in the art. The first oncogenes associated with tumours were described for melanomas. The MAGE (melanoma-associated gene) products were shown to be spontaneously expressed by tumour cells in the context of MHC class I determinants, and as such, recognised by CD8+ cytolytic T cells. However, MAGE-derived antigens, such as MAGE-3, are also expressed in MHC class II determinants and CD4+ specific T cells have been cloned from melanoma patients (Schutz et al. (2000) *Cancer Research* 60: 6272-6275; Schuler-Thurner et al. (2002) *J. Exp. Med.* 195: 1279-1288). Peptides presented by MHC class II determinants are known in the art. Other examples include the gp100 antigen expressed by the P815 mastocytoma and by melanoma cells (Lapointe (2001) *J. Immunol.* 167: 4758-4764; Cochlovius et al. (1999) *Int. J. Cancer,* 83: 547-554).

Proto-oncogenes include a number of polypeptides and proteins which are preferentially expressed in tumours cells, and only minimally in healthy tissues. Cyclin D1 is cell cycle regulator which is involved in the G1 to S transition. High expression of cyclin D1 has been demonstrated in renal cell carcinoma, parathyroid carcinomas and multiple myeloma. A peptide encompassing residues 198 to 212 has been shown to carry a T cell epitope recognised in the context of MHC class II determinants (Dengiel et al. (2004) *Eur. J. of Immunol.* 34: 3644-3651).

Survivin is one example of a factor inhibiting apoptosis, thereby conferring an expansion advantage to survivin-expressing cells. Survivin is aberrantly expressed in human cancers of epithelial and hematopoietic origins and not expressed in healthy adult tissues except the thymus, testis and placenta, and in growth-hormone stimulated hematopoietic progenitors and endothelial cells. Interestingly, survivin-specific CD8+ T cells are detectable in blood of melanoma patients. Survivin is expressed by a broad variety of malignant cell lines, including renal carcinoma, breast cancer, and multiple myeloma, but also in acute myeloid leukemia, and in acute and chronic lymphoid leukemia (Schmidt (2003) *Blood* 102: 571-576). Other examples on inhibitors of apoptosis are Bcl2 and spi6.

Idiotypic determinants are presented by B cells in follicular lymphomas, multiple myeloma and some forms of leukemia, and by T cell lymphomas and some T cell leukemias. Idiotypic determinants are part of the antigen-specific receptor of either the B cell receptor (BCR) or the T cell receptor (TCR). Such determinants are essentially encoded by hypervariable regions of the receptor, corresponding to complementarity-determining regions (CDR) of either the VH or VL regions in B cells, or the CDR3 of the beta chain in T cells. As receptors are created by the random rearrangement of genes, they are unique to each individual. Peptides derived from idiotypic determinants are presented in MHC class II determinants (Baskar et al. (2004) *J. Clin. Invest.* 113: 1498-1510). Some tumours are associated with expression of virus-derived antigens. Thus, some forms of Hodgkin disease express antigens from the Epstein-Barr virus (EBV). Such antigens are expressed in both class I and class II determinants. CD8+ cytolytic T cells specific for EBV antigens can eliminate Hodgkin lymphoma cells (Bollard et al. (2004) *J. Exp. Med.* 200: 1623-1633). Antigenic determinants such as LMP-1 and LMP-2 are presented by MHC class II determinants.

A minimum requirement for the cytotoxic CD4+ T-cells to be activated is to recognise a cognate tumour-associated antigen-derived epitope presented by MHC class II determinants, leading to apoptosis of the APC. Expression of MHC class II determinants by tumour cells is likely to be much more frequent than previously thought. Thus, malignant cells derived from the hematopoietic lineages and cells derived from endothelium or epithelium progenitors express class II determinants. In addition, expression of such determinants can be induced by inflammatory conditions that often prevail in tumours, as a result of the production of cytokines such as IFN-gamma or TNF-alpha by host cells.

There may be situations in which more than one tumour-associated antigen exists in a given tumour or tumour cell. It is therefore anticipated that combination of two or more immunogenic peptides may be used for the treatment of a tumour or for the treatment or prevention of a tumour relapse.

In any of the uses and methods described hereinabove, the one or more immunogenic peptides can be replaced by CD4+ regulatory T-cells (Tregs) primed with the immunogenic peptide(s) (i.e., adoptive cell transfer), or can be replaced by a nucleotide sequence encoding the immunogenic peptide(s) (e.g. in the form of naked DNA or a viral vector to be administered to an individual instead of the immunogenic peptide). In particular, both active immunisation with immunogenic peptides and adoptive cell transfer of in vitro expanded Tregs can be envisaged for antigens which are associated with tumours and not with normal cells, namely oncogenes such as MAGE, idiotypic determinants and perhaps some virus proteins. For tumour-associated antigens which are overexpressed in tumours but also present in healthy cells, adoptive cell transfer may be the preferred option. It is further feasible to target tumour cells by gene therapy, so as to express a given immunogenic peptide according to the invention only in tumour cells. In such a scenario, any tumour antigen can be used as starting point for designing an immunogenic peptide according to the invention. In addition, a combination of multiple immunogenic peptides, i.e. more than 1 (e.g., 2, 3, 4, 5, 6, 7, 8, 9, 10 or more), can be used in the above-described applications. These aspects of the invention, as well as the further modification of the immunogenic peptides are described in detail hereafter.

The present invention is based upon the finding that an immunogenic peptide, comprising a T cell epitope derived from a tumour-associated antigen and a peptide sequence, having reducing activity is capable of generating a population of CD4+ regulatory T cells, which have a cytotoxic effect on tumour-associated antigen presenting cells.

Accordingly, the invention relates to immunogenic peptides, which comprise at least one T-cell epitope of a tumour-associated antigen with a potential to trigger an immune reaction, coupled to an organic compound having a reducing activity, such as a thioreductase sequence motif. The T cell epitope and the organic compound are optionally separated by a linker sequence. In further optional embodiments the immunogenic peptide additionally comprises an endosome targeting sequence (e.g. late endosomal targeting sequence) and/or additional "flanking" sequences.

The immunogenic peptides of the invention can be schematically represented as A-L-B or B-L-A, wherein A represents a T-cell epitope of an antigen (self or non-self) with a potential to trigger an immune reaction, L represents a linker and B represents an organic compound having a reducing activity.

The reducing activity of an organic compound can be assayed for its ability to reduce a sulfhydryl group such as in the insulin solubility assay known in the art, wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxidoreductases They exert reducing activity for disulfide bonds on proteins (such as enzymes) through redox active cysteines within conserved active domain consensus sequences: C-X(2)-C, C-X(2)-S, C-X(2)-T, S-X(2)-C, T-X(2)-C (Fomenko et al. (2003) *Biochemistry* 42, 11214-11225), in which X stands for any amino acid. Such domains are also found in larger proteins such as protein disulfide isomerase (PDI) and phosphoinositide-specific phospholipase C.

Accordingly, in particular embodiments, immunogenic peptides according to the present invention comprise as redox motif the thioreductase sequence motif [CST]-X(2)-[CST], in a further embodiment thereto, said [CST]-X(2)-[CST] motif is positioned N-terminally of the T-cell epitope. More specifically, in said redox motif at least one of the [CST] positions is occupied by a Cys; thus the motif is either [C]-X(2)-[CST] or [CST]-X(2)-[C]. In the present application such a tetrapeptide will be referred to as "the motif". In particular embodiments peptides of the invention contain the sequence motif [C]-X(2)-[CS] or [CS]-X(2)-[C]. In more particular embodiments peptides contain the sequence motif C-X(2)-S, S-X(2)-C or C-X(2)-C.

As explained in detail further on, the immunogenic peptides of the present invention can be made by chemical synthesis, which allows the incorporation of non-natural amino acids. Accordingly, in the motif of reducing compounds according to particular embodiments of the present invention, C represents either cysteine or another amino acids with a thiol group such as mercaptovaline, homocysteine or other natural or non-natural amino acids with a thiol function. In order to have reducing activity, the cysteines present in the motif should not occur as part of a cystine disulfide bridge. Nevertheless, the motif may comprise modified cysteines such as methylated cysteine, which is converted into cysteine with free thiol groups in vivo.

In particular embodiments of the invention, either of the amino acids X in the [CST]-X(2)-[CST] motif of the immunogenic peptides of the invention can be any natural amino acid, including S, C, or T or can be a non-natural amino acid. In particular embodiments X is an amino acid with a small side chain such as Gly, Ala, Ser or Thr. In further particular embodiments, X is not an amino acid with a bulky side chain such as Tyr. In further particular embodiments at least one X in the [CST]-X(2)-[CST] motif is His or Pro.

In the immunogenic peptides of the present invention comprising the (redox) motif described above, the motif is located such that, when the epitope fits into the MHC groove, the motif remains outside of the MHC binding groove. The motif is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 6, 8 or 10 amino acids. Typical amino acids used in linkers are serine and threonine. Example of peptides with linkers in accordance with the present invention are CXXC-G-epitope (SEQ ID NO:9), CXXC-GG-epitope (SEQ ID NO:10), CXXC-SSS-epitope (SEQ ID NO:11), CXXC-SGSG-epitope (SEQ ID NO:12) and the like.

In those particular embodiments of the peptides of the invention where the motif sequence is adjacent to the epitope sequence this is indicated as position P−4 to P−1 or P+1 to P+4 compared to the epitope sequence. Apart from a peptide linker other organic compounds can be used as linker to link the parts of the immunogenic peptide to each other.

The immunogenic peptides of the present invention can further comprise additional short amino acid sequences N or C-terminally of the (artificial) sequence comprising the T cell epitope and the reducing compound (motif). Such an amino acid sequence is generally referred to herein as a 'flanking sequence'. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids.

In particular embodiments of the invention, the redox motif in the immunogenic peptide is located N-terminally from the epitope.

In further particular embodiments, where the redox motif present in the immunogenic peptide contains one cysteine, this cysteine is present in the motif in the position most remote from the epitope, thus the motif occurs as C-X(2)-[ST] or C-X(2)-S N-terminally of the epitope or occurs as [ST]-X(2)-C or S-X(2)-C carboxy-terminally of the epitope.

In certain embodiments of the present invention, immunogenic peptides are provided comprising one epitope sequence and a motif sequence. In further particular embodiments, the motif occurs several times (1, 2, 3, 4 or even more times) in the peptide, for example as repeats of the motif which can be spaced from each other by one or more amino acids (e.g. CXXC X CXXC X CXXC; SEQ ID NO:13), as repeats which are adjacent to each other (CXXC CXXC CXXC; SEQ ID NO:14) or as repeats which overlap with each other CXX- CXXCXXC (SEQ ID NO:15) or CXCCXCCXCC (SEQ ID NO:16)). Alternatively, one or more motifs are provided at both the N and the C terminus of the T cell epitope sequence. Other variations envisaged for the immunogenic peptides of the present invention include peptides containing repeats of a T cell epitope sequence or multiple different T-cell epitopes wherein each epitope is preceded and/or followed by the motif (e.g. repeats of "motif-epitope" or repeats of "motif-epitope-motif"). Herein the motifs can all have the same sequence but this is not obligatory. It is noted that repetitive sequences of peptides which comprise an epitope which in itself comprises the motif will also result in a sequence comprising both the 'epitope' and a 'motif'. In such peptides, the motif within one epitope sequence functions as a motif outside a second epitope sequence. In particular embodiments however, the immunogenic peptides of the present invention comprise only one T cell epitope.

As described above the immunogenic peptides according to the invention comprise, in addition to a reducing compound/motif, a T cell epitope derived from a tumour-associated antigen. A T cell epitope in a protein sequence can be identified by functional assays and/or one or more in silico prediction assays. The amino acids in a T cell epitope sequence are numbered according to their position in the binding groove of the MHC proteins. In particular embodiments, the T-cell epitope present within the peptides of the invention consists of between 8 and 25 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 9 amino acids. In a further particular embodiment, the T-cell epitope is an epitope, which is presented to T cells by MHC-class II molecules. In particular embodiments of the present invention, the T cell epitope sequence is an epitope sequence which fits into the cleft of an MHC II protein, more particularly a nonapeptide fitting into the MHC II cleft. The T cell epitope of the immunogenic peptides of the invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilising effect on protein complexes. Accordingly, the stabilising effect of the peptide-MHC complex compensates for the lowered affinity of the modified epitope for the MHC molecule.

In particular embodiments, the immunogenic peptides of the invention further comprise an amino acid sequence (or another organic compound) facilitating uptake of the peptide into (late) endosomes for processing and presentation within MHC class II determinants. The late endosome targeting is mediated by signals present in the cytoplasmic tail of proteins and correspond to well-identified peptide motifs such as the dileucine-based [DE]XXXL[LI] (SEQ ID NO:17) or DXXLL (SEQ ID NO:18) motif (e.g. DXXXLL; SEQ ID NO:19), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J Cell Biol* 130, 807-820), the human CD3 gamma protein, the HLA-BM β (Copier et al. (1996) *J. lmmunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the tumour-associated antigen -derived T cell epitope.

The immunogenic peptides of the invention can be generated by coupling a reducing compound, more particularly a reducing motif as described herein, N-terminally or C-terminally to a T-cell epitope of the tumour-associated antigen (either directly adjacent thereto or separated by a linker). Moreover the T cell epitope sequence of the immunogenic peptide and/or the redox motif can be modified and/or one or more flanking sequences and/or a targeting sequence can be introduced (or modified), compared to the naturally occurring T-cell epitope sequence. Accordingly, the resulting sequence of the immunogenic peptide will in most cases differ from the sequence of the tumour-associated antigen protein of interest. In this case, the immunogenic peptides of the invention are peptides with an 'artificial', non-naturally occurring sequence.

The immunogenic peptides of the invention can vary substantially in length, e.g. from about 12-13 amino acids (a T-cell epitope of 8-9 amino acids and the 4-amino acid redox motif) to up to 50 or more amino acids. For example, an immunogenic peptide according to the invention may comprise an endosomal targeting sequence of 40 amino acids, a flanking sequence of about 2 amino acids, a motif as described herein of 4 amino acids, a linker of 4 amino acids and a T cell epitope peptide of 9 amino acids. In particular embodiments, the immunogenic peptides of the invention consist of between 12 amino acids and 20 up to 25, 30, 50, 75, 100 or 200 amino acids. In a more particular embodiment, the peptides consist of between 10 and 20 amino acids. More particularly, where the reducing compound is a redox motif as described herein, the length of the immunogenic peptide comprising the epitope and motif optionally connected by a linker is 18 amino acids or less, e.g., 12, 13, 14, 15, 16, 17, 18 or 19 amino acids.

As detailed above, the immunogenic peptides of the invention comprise a reducing motif as described herein linked to a T cell epitope sequence. According to particular embodiments the T-cell epitopes are derived from tumour-associated antigens which do not comprise within their native natural sequence an amino acid sequence with redox properties within a sequence of 11 amino acids N- or C-terminally adjacent to the T-cell epitope of interest. Most particularly, the invention encompasses generating immunogenic peptides from tumour-associated antigens which do not comprise a sequence selected from C-X(2)-S, S-X(2)-C, C-X(2)-C, S-X(2)-S, C-X(2)-T, T-X(2)-C within a sequence of 11 amino acids N- or C-terminally adjacent to the epitope sequence. In further particular embodiments, the present invention provides immunogenic peptides of tumour-associated antigens which do not comprise the above-described amino acid sequences with redox properties within their sequence.

In further particular embodiments, the immunogenic peptides of the invention are peptides comprising T cell epitopes which T cell epitopes do not comprise an amino acid sequence with redox properties within their natural sequence.

However, in alternative embodiments, a T cell epitope binding to the MHC cleft may comprise a redox motif such as described herein within its epitope sequence; the immunogenic peptides according to the invention comprising such a T-cell epitope must further comprise another redox motif coupled (adjacent of separated by a linker) N- or C-terminally to the epitope such that the attached motif can ensure the reducing activity (contrary to the motif present in the epitope, which is buried within the cleft).

Another aspect of the present invention relates to methods for generating immunogenic peptides of the present invention described herein. Such methods include the identification of T-cell epitopes in a tumour-associated antigen of interest; ways for in vitro and in silico identification T-cell epitopes are amply known in the art and some aspects are elaborated upon hereafter. In particular embodiments, methods according to the invention further include the generation of immunogenic peptides of the invention (including the identified T-cell epitope and a redox motif (with or without linker(s), flanking sequence(s) or endosomal targeting sequence)). The generated immunogenic peptides may be assessed for the capability to induce tumour-associated antigen-specific CD4+ regulatory T cells which are cytotoxic for cells presenting (parts of) the tumour-associated antigen of interest.

Immunogenic peptides according to the invention are generated starting from T cell epitope(s) of the tumour-associated antigen(s) of interest. In particular, the T-cell epitope used may be a dominant T-cell epitope. The identification and selection of a T-cell epitope from a tumour-associated antigen, for use in the context of the present invention is known to a person skilled in the art. For instance, peptide sequences isolated from a tumour-associated antigen are tested by, for example, T cell biology techniques, to determine whether the peptide sequences elicit a T cell response. Those peptide sequences found to elicit a T cell response are defined as having T cell stimulating activity. Human T cell stimulating activity can further be tested by culturing T cells obtained from an individual sensitised to a tumour-associated antigen with a peptide/epitope derived from the tumour-associated antigen and determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested. Non-natural (or modified) T-cell epitopes can further optionally be tested for their binding affinity to MHC class II molecules. The binding of non-natural (or modified) T-cell epitopes to MHC class II molecules can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184). The immunogenic peptides of the invention have a mean T cell stimulation index of greater than or equal to 2.0. An immunogenic peptide having a T cell stimulation index of greater than or equal to 2.0 is considered useful as a prophylactic or therapeutic agent. More particularly, immunogenic peptides according to the invention have a mean T cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean T cell stimulation index by the percent of individuals, in a population of individuals sensitive to a tumour-associated antigen (e. g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to a tumour-associated antigen. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Candidate antigens can be screened by one or more in vitro algorithms to identify a T cell epitope sequence within an antigenic protein. Suitable algorithms are described for example in Zhang et al. (2005) *Nucleic Acids Res* 33, W180-W183 (PREDBALB); Salomon & Flower (2006) *BMC Bioinformatics* 7, 501 (MHCBN); Schuler et al. (2007) *Methods Mol Biol.* 409, 75-93 (SYFPEITHI); Dönnes & Kohlbacher (2006) *Nucleic Acids Res.* 34, W194-W197 (SVMHC); Kolaskar & Tongaonkar (1990) *FEBS Lett.* 276, 172-174 and Guan et al. (2003) *Appl Bioinformatics* 2, 63-66 (MHCPred). More particularly, such algorithms allow the prediction within an antigenic protein of one or more nonapeptide sequences which will fit into the groove of an MHC II molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves standard recombinant DNA techniques. Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205. This provides the tremendous potential to achieve protein synthesis which is beyond the scope of SPPS. Many proteins with the size of 100-300 residues have been synthesised successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) is examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

Accordingly, in yet a further aspect, the present invention provides methods for generating tumour-associated antigen-specific cytotoxic T cells (Tregs or CD4+ regulatory T-cells) either in vivo or in vitro (ex vivo). In particular said T cells are cytotoxic towards any cell presenting a tumour-associated antigen and are obtainable as a cell population. The invention extends to such (populations of) tumour-associated antigen cytotoxic Tregs obtainable by the herein described methods.

In particular embodiments, methods are provided which comprise the isolation of peripheral blood cells, the stimulation of the cell population in vitro by contacting an immunogenic peptide according to the invention with the isolated peripheral blood cells, and the expansion of the stimulated cell population, more particularly in the presence of IL-2. The methods according to the invention have the advantage that higher numbers of Tregs are produced and that the Tregs can be generated which are specific for the tumour-associated antigen (by using a peptide comprising an antigen-specific epitope). Alternatively, tumour-associated antigen-specific cytotoxic T cells may be obtained by incubation in the presence of APCs presenting a tumour-associated antigen-specific immunogenic peptide according to the invention after transduction or transfection of the APCs with a genetic construct capable of driving expression of such immunogenic peptide. Such APCs may in fact themselves be administered to a subject in need to trigger in vivo in said subject the induction of the beneficial subset of cytotoxic CD4+ T-cells.

In an alternative embodiment, the Tregs can be generated in vivo, i.e. by the administration of an immunogenic peptide provided herein to a subject, and collection of the Tregs generated in vivo.

The tumour-associated antigen-specific regulatory T cells obtainable by the above methods are of particular interest for use in the manufacture of a medicament for treating a tumour or for preventing or treating a tumour relapse, i.e., for any of the above-described uses of the immunogenic peptides of the invention, said peptides can be replaced by said tumour-associated antigen-specific Tregs. Both the use of allogeneic and autogeneic cells is envisaged. Any method comprising the administration of said tumour-associated antigen-specific Tregs to a subject in need (i.e., for treating a tumour or for preventing or treating a tumour relapse) is also known as adoptive cell therapy. Tregs are crucial in immunoregulation and have great therapeutic potential. The efficacy of Treg-based immunotherapy depends on the Ag specificity of the regulatory T cells. Moreover, the use of Ag-specific Treg as opposed to polyclonal expanded Treg reduces the total number of Treg necessary for therapy.

The present invention also relates to nucleic acid sequences encoding the immunogenic peptides of the present invention and methods for their use, e.g., for recombinant expression or in gene therapy. In particular, said nucleic acid sequences are capable of expressing an immunogenic peptides of the invention.

The immunogenic peptides of the invention may indeed be administered to a subject in need by using any suitable gene therapy method. In any use or method of the invention for the treatment of a tumour and/or for treatment or prevention of a tumour relapse, immunisation with an immunogenic peptide of the invention may be combined with adoptive cell transfer of (a population of) Tregs specific for said immunogenic peptide and/or with gene therapy. When combined, said immunisation, adoptive cell transfer and gene therapy can be used concurrently, or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

The medicament of the invention is usually, but not necessarily, a (pharmaceutical) formulation comprising as active ingredient at least one of the immunogenic peptides of the invention, a (population of) Tregs specific for said immunogenic peptide or a gene therapeutic vector capable of expressing said immunogenic peptide. Apart from the active ingredient(s), such formulation will comprise at least one of a (pharmaceutically acceptable) diluent, carrier or adjuvant. Typically, pharmaceutically acceptable compounds (such as diluents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g.,weight, age), the status of the condition to be prevented or treated, and the experience of the treating doctor, physician or nurse.

The term "diluents" refers for instance to physiological saline solutions. The term "adjuvant" usually refers to a pharmacological or immunological agent that modifies (preferably increases) the effect of other agents (e.g., drugs, vaccines) while having few if any direct effects when given by themselves. As one example of an adjuvant aluminium hydroxide (alum) is given, to which an immunogenic peptide of the invention can be adsorbed. Further, many other adjuvants are known in the art and can be used provided they facilitate peptide presentation in MHC-class II presentation and T cell activation. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Immunogenic peptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

A further aspect of the invention relates to isolated immunogenic peptides comprising a T-cell epitope from a tumour-associated antigen and, adjacent to said T-cell epitope or separated from said T-cell epitope by a linker, a [CST]-(X)2-[CST] motif, more particularly a C-(X)2-[CST] or [CST]-(X)2-C motif. In particular embodiments, the tumour-associated antigen is selected from the group consisting of oncogenes, viral antigens, surviving factors and clonotypic/idiotypic determinants. In further particular embodiments the epitope is an epitope whereby the tumour associated antigen does not naturally comprise within a sequence of 11 amino acids N- or C-terminally adjacent to said epitope, a redox motif. Illustrative examples of tumour associated antigens for which immunogenic peptides are envisaged are mentioned below.

An idiotype is made of the ensemble of antigenic determinants carried by the variable part of antibodies and, as described above, these determinants are reiterated in BCR (corresponding to CDRs) and TCR (corresponding to CDR3). BCR of a B-cell and the antibodies secreted by the same B-cell share idiotypic determinants. During uptake of polypeptides or proteins by B cells, parts of the BCR are processed together with the antigen and are presented by MHC class II determinants. In tumour B-cells such as B cell lymphomas or myelomas, the B-cell receptor (or BCR) is most often directed towards an antigen of undetermined specificity (for example the MGUS syndrome: monoclonal gammopathy of unknown specificity). Hence a strategy to treat such types of tumours or tumour cells comprises the induction (by immunisation and/or gene therapy) of CD4+ regulatory T-cells cytotoxic towards tumour BCR T-cell epitopes (or an idiotope thereof; together referred to hereinafter as tumour B-cell idiotype) or T-cell CDR3 T-cell epitope, and/or adoptive transfer of said cytotoxic CD4+ regulatory T-cells. Indeed, as T-cell epitopes modified by attaching a redox motif thereto induce CD4+ T-cells to acquire the property of inducing apoptosis in APCs presenting said T-cell epitope (natural or modified), tumour B-cell BCR T-cell epitopes (or an idiotope thereof) or tumour T-cell CDR3 T-cell epitope modified by attaching a redox motif thereto are capable of inducing CD4+ T-cells that can drive said tumour B-cells or tumour T-cells into apoptosis.

Hence, a further aspect of the invention relates to the use of at least one isolated immunogenic peptide comprising (i) a T-cell epitope derived from a tumour B-cell idiotype and (ii) a [CST]-(X)2-[CST] motif, more particularly a C-(X)2-[CST] or [CST]-(X)2-C motif, for the manufacture of a medicament for (substantially) treating or preventing a B-cell tumour or relapse of such B-cell tumour.

The invention further relates to the use of at least one isolated immunogenic peptide comprising (i) a T-cell epitope derived from a tumour B-cell idiotype and (ii) a [CST]-(X)2-[CST] motif, more particularly a C-(X)2-[CST] or [CST]-(X)2-C motif, for the manufacture of a medicament for inducing in a recipient CD4+ regulatory T cells which are cytotoxic to said tumour B-cell.

Yet another aspect of the invention relates to the use of at least one isolated immunogenic peptide comprising (i) a T-cell epitope derived from a tumour T-cell CDR3 and (ii) a [CST]-(X)2-[CST] motif, more particularly a C-(X)2-[CST] or [CST]-(X)2-C motif, for the manufacture of a medicament for (substantially) treating or preventing a T-cell tumour or relapse of such T-cell tumour.

The invention further relates to the use of at least one isolated immunogenic peptide comprising (i) a T-cell epitope derived from a tumour T-cell CDR3 and (ii) a [CST]-(X)2-[CST] motif, for the manufacture of a medicament for inducing in a recipient CD4+ regulatory T cells which are cytotoxic to said tumour T-cell.

Further particular embodiments of the invention relate to methods of treating patients suffering from a tumour expressing a viral antigen, which methods comprise, administering to the patient, an immunogenic peptide according to the invention comprising a T-cell epitope against the viral antigen and a redox motif as described herein. In particular embodiments the viral antigen is an antigen of a virus selected from the group consisting of herpes viruses, C-type viruses an B-type RNA mammary tumour viruses.

The present invention will now be illustrated by means of the following examples, which are provided without any limiting intention. Furthermore, all references described herein are explicitly included herein by reference.

EXAMPLES

Example 1

Cytotoxic Regulatory CD4+ T Cells are Elicited by in Vivo Immunisation with a Peptide Comprising a Melanoma-Associated Antigen (MAGE-3) T Cell Epitope to Which a Thioreductase Consensus Sequence is Added C57Bl/6 mice (group 1) are immunised with 25 µg of a peptide containing a (natural) T cell epitope of MAGE-3 by 3 footpath injections in CFA/IFA made at a fortnight interval. The sequence of the (natural) T-cell epitope corresponds to amino acids 258 to 266 of MAGE-3, namely: YRQVPGSDP (SEQ ID NO:1).

A second group of C57Bl/6 mice (group 2) are immunised using the same protocol with the peptide of SEQ ID NO:1 to which a consensus motif exhibiting thioreductase activity (or shortly: redox motif) was added at the amino-terminal end, namely: CHGCYRQVPGSDP (SEQ ID NO:2; redox motif underlined; modified T-cell epitope)

Ten days after the last immunisation, the spleens of all mice are recovered and CD4+ T cells are prepared by sorting on magnetic beads.

Spleen adherent cells prepared from naïve C57Bl/6 mice are used as antigen-presenting cells (APC). Such APC ($2 \times 10^7$) are loaded with either peptide of SEQ ID NO:1 or peptide of SEQ ID NO:2 (5 µg/mL) by an 1-h incubation followed by a wash.

CD4+ T cells obtained from either group 1 or group 2 mice are added to the population of APCs and co-cultured for 24 h at 37° C. Cells are then recovered and incubated with a fluorescent-labelled anti-CD11c antibody and with FITC-labelled annexin V as a marker of apoptosis. Finally, cells are analysed by Facs analysis.

These experiments demonstrate that a peptide of SEQ ID NO:2 can elicit CD4+ T cells with cytotoxic properties towards APCs presenting either the natural MAGE-3 T-cell epitope (SEQ ID NO:1) or the modified MAGE-3 T-cell epitope (SEQ ID NO:2).

Example 2

Cytotoxic Regulatory CD4+ T Cells are Elicited by in Vivo Immunisation with a Peptide Comprising a Cyclin D1 T-Cell Epitope to Which a Thioreductase Consensus Sequence is Added C57Bl/6 mice (group 1) are immunised with 25 μg of a peptide containing a (natural) T-cell epitope of cyclin D1 by 3 footpath injections in CFA/IFA made at a fortnight interval. The sequence of the peptide corresponds to amino acids 185 to 193 of cyclin D1, namely: FVALCATDV (SEQ ID NO:3).

A second group of C57Bl/6 mice (group 2) are immunized using the same protocol as above but with peptide of SEQ ID NO:3 to which a consensus motif exhibiting thioreductase activity (or shortly: redox motif) is added at the amino-terminal end, namely: CHGCFVALCATDV (SEQ ID NO:4; redox motif underlined; modified T-cell epitope).

Ten days after the last immunisation, the spleens of all mice are recovered and CD4+ T cells are prepared by sorting on magnetic beads.

Spleen adherent cells prepared from naïve C57Bl/6 mice are used as antigen-presenting cells (APC). Such APC ($2\times10^7$) are loaded with either peptide of SEQ ID NO:3 or peptide of SEQ ID NO:4 (5 μg/mL) by an 1-h incubation followed by a wash.

CD4+ T cells obtained from either group 1 or group 2 mice are added to the population of APCs and co-cultured for 24 h at 37° C. Cells are then recovered and incubated with a fluorescent-labelled anti-CD11c antibody and with FITC-labelled annexin V as a marker of apoptosis. Finally, cells are analysed by Facs analysis.

These experiments demonstrate that a peptide of SEQ ID NO:4 can elicit CD4+ T cells with cytotoxic properties towards APCs presenting either the natural cyclin D1 T-cell epitope (SEQ ID NO:3) or the modified cyclin D1 T-cell epitope (SEQ ID NO:4).

Example 3

Cytotoxic Regulatory CD4+ T Cells are Elicited by in Vivo Immunisation with a Peptide Comprising a Survivin T Cell Epitope to Which a Thioreductase Consensus Sequence is Added C57Bl/6 mice (group 1) are immunised with 25 μg of a peptide containing a (natural) T cell epitope of survivin by 3 footpath injections in CFA/IFA made at a fortnight interval. The sequence of the peptide corresponds to amino acids 61 to 69 of survivin, namely: FKELEGWEP (SEQ ID NO:5).

A second group of C57Bl/6 mice (group 2) are immunised using the same protocol with peptide of SEQ ID NO:5 to which a consensus motif exhibiting thioreductase activity (or shortly: redox motif) was added at the amino-terminal end, namely: CHGCFKELEGWEP (SEQ ID NO:6; redox motif underlined; modified T-cell epitope).

Ten days after the last immunisation, the spleens of all mice are recovered and CD4+ T cells are prepared by sorting on magnetic beads.

Spleen adherent cells prepared from naïve C57Bl/6 mice are used as antigen-presenting cells (APC). Such APC ($2\times10^7$) are loaded with either peptide of SEQ ID NO:5 or peptide of SEQ ID NO:6 (5 μg/mL) by an 1-h incubation followed by a wash.

CD4+ T cells obtained from either group 1 or group 2 mice are added to the population of APCs and co-cultured for 24 h at 37° C. Cells are then recovered and incubated with a fluorescent-labelled anti-CD11c antibody and with FITC-labelled annexin V as a marker of apoptosis. Finally, cells are analysed by Facs analysis.

These experiments demonstrate that a peptide of SEQ ID NO:6 can elicit CD4+ T cells with cytotoxic properties towards APCs presenting either the natural survivin T-cell epitope (SEQ ID NO:5) or the modified survivin T-cell epitope (SEQ ID NO:6).

Example 4

Cytotoxic Regulatory CD4+ T Cells are Elicited by in Vivo Immunisation with a Peptide Comprising an Epstein-Barr LMP2 T Cell Epitope to Which a Thioreductase Consensus Sequence is Added BALB/c mice (group 1) are immunised with 25 μg of a peptide containing a (natural) T cell epitope of LMP2 from the Epstein-Barr virus by 3 footpath injections in CFA/IFA made at a fortnight interval. The sequence of the peptide corresponds to amino acids 167 to 175 of LMP2, namely: VASSYAAAQ (SEQ ID NO:7).

A second group of BALB/c mice (group 2) are immunised using the same protocol with peptide of SEQ ID NO:7 to which a consensus motif exhibiting thioreductase activity (or shortly: redox motif) is added at the amino-terminal end, namely: CHGCVASSYAAAQ (SEQ ID NO:8; redox motif underlined; modified T-cell epitope).

Ten days after the last immunisation, the spleens of all mice are recovered and CD4+ T cells are prepared by sorting on magnetic beads.

Spleen adherent cells prepared from naïve BALB/c mice are used as antigen-presenting cells (APC). Such APC ($2\times10^7$) are loaded with either peptide of SEQ ID NO:7 or peptide of SEQ ID NO:8 (5 μg/mL) by an 1-h incubation followed by a wash.

CD4+ T cells obtained from either group 1 or group 2 mice are added to the population of APCs and co-cultured for 24 h at 37° C. Cells are then recovered and incubated with a fluorescent-labelled anti-CD11c antibody and with FITC-labelled annexin V as a marker of apoptosis. Finally, cells are analysed by Facs analysis.

These experiments demonstrate that a peptide of SEQ ID NO:8 can elicit CD4+ T cells with cytotoxic properties towards APCs presenting either the natural Epstein-Barr LMP2 T-cell epitope (SEQ ID NO:7) or the modified Epstein-Barr LMP2 T-cell epitope (SEQ ID NO:8).

The invention claimed is:

1. A method of treating a tumor expressing a tumor associated antigen or of treating a relapse of a tumor expressing a tumor associated antigen comprising the step of administering, an immunogenic fusion peptide consisting of between 13 and 50 amino acids, comprising (i) an MHC Class II restricted T-cell epitope consisting of 8 or 9 amino acids of said tumor-associated antigen and (ii) a reducing C-(X)2-C motif, wherein X is not cysteine, which motif is separated from said T-cell epitope by a linker consisting of 1 or 2 amino acids.

2. The method of claim 1, wherein said treatment induces CD4+ T cells which are cytotoxic to cells presenting said tumor-associated antigen.

3. The method according to claim 1 wherein said tumor-associated antigen is an oncogene, a proto-oncogene, a viral protein, a surviving factor or a clonotypic determinant.

4. The method according to claim 1 wherein said immunogenic peptide further comprises an endosomal targeting sequence.

5. The method according to claim 1 wherein said C-(X)2-C motif is positioned N-terminally of the T-cell epitope.

6. The method according to claim 1 wherein at least one X in said C-(X)2-C motif is Gly, Ala, Ser or Thr.

7. The method according to claim 1 wherein at least one X in said C-(X)2-C motif is His or Pro.

8. The method according to claim 1 wherein at least one C in said C-(X)2-C motif is methylated.

9. The method according to claim 1 wherein said immunogenic peptide is produced by chemical synthesis or by recombinant expression.

* * * * *

SEQUENCE LISTING

<160> NUMBER OF SEQ ID NOS: 19

<210> SEQ ID NO 1
<211> LENGTH: 9
<212> TYPE: PRT
<213> ORGANISM: Artificial Sequence

```
<220> FEATURE:
<223> OTHER INFORMATION: amino acids 258-266 of MAGE-3

<400> SEQUENCE: 1

Tyr Arg Gln Val Pro Gly Ser Asp Pro
1               5

<210> SEQ ID NO 2
<211> LENGTH: 13
<212> TYPE: PRT
<213> ORGANISM: Artificial Sequence
<220> FEATURE:
<223> OTHER INFORMATION: modified T-cell epitope of MAGE-3
<220> FEATURE:
<221> NAME/KEY: MISC_FEATURE
<222> LOCATION: (1)..(4)
<223> OTHER INFORMATION: thioreductase motif

<400> SEQUENCE: 2

Cys His Gly Cys Tyr Arg Gln Val Pro Gly Ser Asp Pro
1               5                   10

<210> SEQ ID NO 3
<211> LENGTH: 9
<212> TYPE: PRT
<213> ORGANISM: Artificial Sequence
<220> FEATURE:
<223> OTHER INFORMATION: amino acids 185-193 of cyclin D1

<400> SEQUENCE: 3

Phe Val Ala Leu Cys Ala Thr Asp Val
1               5

<210> SEQ ID NO 4
<211> LENGTH: 13
<212> TYPE: PRT
<213> ORGANISM: Artificial Sequence
<220> FEATURE:
<223> OTHER INFORMATION: modified T-cell epitope of cyclin D1
<220> FEATURE:
<221> NAME/KEY: MISC_FEATURE
<222> LOCATION: (1)..(4)
<223> OTHER INFORMATION: thioreductase motif

<400> SEQUENCE: 4

Cys His Gly Cys Phe Val Ala Leu Cys Ala Thr Asp Val
1               5                   10

<210> SEQ ID NO 5
<211> LENGTH: 9
<212> TYPE: PRT
<213> ORGANISM: Artificial Sequence
<220> FEATURE:
<223> OTHER INFORMATION: amino acids 61-69 of survivin

<400> SEQUENCE: 5

Phe Lys Glu Leu Glu Gly Trp Glu Pro
1               5

<210> SEQ ID NO 6
<211> LENGTH: 13
<212> TYPE: PRT
<213> ORGANISM: Artificial Sequence
<220> FEATURE:
<223> OTHER INFORMATION: modified T-cell epitope of survivin
<220> FEATURE:
<221> NAME/KEY: MISC_FEATURE
<222> LOCATION: (1)..(4)
<223> OTHER INFORMATION: thioreductase motif
```

-continued

<400> SEQUENCE: 6

Cys His Gly Cys Phe Lys Glu Leu Glu Gly Trp Glu Pro
1               5                   10

<210> SEQ ID NO 7
<211> LENGTH: 9
<212> TYPE: PRT
<213> ORGANISM: Artificial Sequence
<220> FEATURE:
<223> OTHER INFORMATION: amino acids 167-175 of LMP2 of Epstein-Barr
      virus

<400> SEQUENCE: 7

Val Ala Ser Ser Tyr Ala Ala Ala Gln
1               5

<210> SEQ ID NO 8
<211> LENGTH: 13
<212> TYPE: PRT
<213> ORGANISM: Artificial Sequence
<220> FEATURE:
<223> OTHER INFORMATION: modified T-cell epitope of LMP2 of Epstein-Barr
      virus
<220> FEATURE:
<221> NAME/KEY: MISC_FEATURE
<222> LOCATION: (1)..(4)
<223> OTHER INFORMATION: thioreductase motif

<400> SEQUENCE: 8

Cys His Gly Cys Val Ala Ser Ser Tyr Ala Ala Ala Gln
1               5                   10

<210> SEQ ID NO 9
<211> LENGTH: 6
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (6)..(6)
<223> OTHER INFORMATION: Xaa denotes the sequence of any T-cell epitope

<400> SEQUENCE: 9

Cys Xaa Xaa Cys Gly Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (7)..(7)
<223> OTHER INFORMATION: Xaa denotes sequence of any T-cell epitope

<400> SEQUENCE: 10

Cys Xaa Xaa Cys Gly Gly Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (8)..(8)
<223> OTHER INFORMATION: Xaa denotes sequence of any T-cell epitope

<400> SEQUENCE: 11

Cys Xaa Xaa Cys Ser Ser Ser Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (9)..(9)
<223> OTHER INFORMATION: Xaa denotes sequence of any T-cell epitope

<400> SEQUENCE: 12

Cys Xaa Xaa Cys Ser Gly Ser Gly Xaa
1               5

<210> SEQ ID NO 13
<211> LENGTH: 14
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(14)
<223> OTHER INFORMATION: Xaa at positions 2, 3, 5, 7, 8, 10, 12, and 13
      denote any amino acid

<400> SEQUENCE: 13

Cys Xaa Xaa Cys Xaa Cys Xaa Xaa Cys Xaa Cys Xaa Xaa Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(12)
<223> OTHER INFORMATION: Xaa at positions 2, 3, 6, 7, 10, and 11 denote
      any amino acid

<400> SEQUENCE: 14

Cys Xaa Xaa Cys Cys Xaa Xaa Cys Cys Xaa Xaa Cys
1               5                   10

```
<210> SEQ ID NO 15
<211> LENGTH: 10
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(10)
<223> OTHER INFORMATION: Xaa at positions 2, 3, 5, 6, 8, and 9 denote
      any amino acid

<400> SEQUENCE: 15

Cys Xaa Xaa Cys Xaa Xaa Cys Xaa Xaa Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(10)
<223> OTHER INFORMATION: Xaa at positions 2, 5, and 8 denote any amino
      acid

<400> SEQUENCE: 16

Cys Xaa Cys Cys Xaa Cys Cys Xaa Cys Cys
1               5                   10

<210> SEQ ID NO 17
<211> LENGTH: 6
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (1)..(1)
<223> OTHER INFORMATION: Xaa denotes aspartate (D or Asp) or glutamate
      (E or Glu)
<220> FEATURE:
<221> NAME/KEY: MISC_FEATURE
<222> LOCATION: (2)..(4)
<223> OTHER INFORMATION: Xaa at positions 2, 3 and 4 denote any amino
      acid
<220> FEATURE:
<221> NAME/KEY: MISC_FEATURE
<222> LOCATION: (6)..(6)
<223> OTHER INFORMATION: Xaa denotes leucine (L or Leu) or isoleucine
      (I or Ile)

<400> SEQUENCE: 17

Xaa Xaa Xaa Xaa Leu Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (2)..(3)
<223> OTHER INFORMATION: Xaa at positions 2 and 3 denote any amino acid

<400> SEQUENCE: 18

Asp Xaa Xaa Leu Leu
```

```
<210> SEQ ID NO 19
<211> LENGTH: 6
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (2)..(5)
<223> OTHER INFORMATION: Xaa at positions 2, 3 and 4 denote any amino
      acid

<400> SEQUENCE: 19

Asp Xaa Xaa Xaa Leu Leu
1               5
```